United States Patent [19]
Connery et al.

[11] 4,333,352
[45] Jun. 8, 1982

[54] INJECTION-MOLDED DOPPLER FLOWMETER TRANSDUCER ASSEMBLY

[75] Inventors: James G. Connery, Ambler; Dominick D. Diascro, Philadelphia; Louis D. DiNapoli, Colmar; Giancarlo Punis, Chalfont; Anthony J. Matour, Harleysville, all of Pa.

[73] Assignee: Leeds & Northrup Company, North Wales, Pa.

[21] Appl. No.: 197,059

[22] Filed: Oct. 14, 1980

[51] Int. Cl.³ .............................................. G01F 1/66
[52] U.S. Cl. .................................. 73/861.18; 73/644; 310/334
[58] Field of Search ................. 73/622, 637, 638, 640, 73/644, 861.18, 861.23, 861.25, 861.26, 861.27, 861.28; 310/334, 348, 354

[56] References Cited
U.S. PATENT DOCUMENTS

| | | | |
|---|---|---|---|
| 3,233,449 | 2/1966 | Harmon | 73/640 X |
| 3,580,092 | 5/1971 | Scarpa | 73/861.18 |
| 3,661,146 | 5/1972 | Peronneau et al. | 73/644 X |
| 3,732,532 | 5/1973 | Flaherty et al. | 73/861.25 X |
| 4,065,958 | 1/1978 | Krylova et al. | 73/861.28 X |
| 4,279,167 | 7/1981 | Erb et al. | 73/861.25 |

Primary Examiner—Charles A. Ruehl
Attorney, Agent, or Firm—Raymond F. MacKay; William G. Miller, Jr.

[57] ABSTRACT

A transducer housing assembly for an ultrasonic flowmeter made by an injection molding having a pair of pedestals for supporting the transducers at a specific angle while acoustically isolating the transducers from each other and providing an air backing for the transducers to improve the sensitivity of the transducer assembly.

14 Claims, 6 Drawing Figures

INJECTION-MOLDED DOPPLER FLOWMETER TRANSDUCER ASSEMBLY

BACKGROUND OF THE INVENTION

Industrial ultrasonic transducer heads secured to the outside of a pipe for determination of the flow of fluids have been constructed as shown in U.S. Pat. No. 4,208,908-Hickox, with the transducers completely imbedded in an epoxy resin and with the surface of the transducer head having a flat surface. Upon mounting of the transducer head to the outer wall of the pipe, there is a line contact between the head and the pipe and the space between the outer wall of the pipe and the flat surface of the transducer head is generally filled with an acoustic couplant or a suitable adhesive such as an epoxy resin.

Such transducer head configuration made it difficult to properly apply the transducer head to the outside wall of the pipe because of the tendency of the flat surface of the transducer head to rock on the round surface of the outer wall of the pipe. Additionally, it was difficult with the imbedding technique to obtain accurate angular alignment of the transducers in their mountings to provide a precise control of the angle of the transducer relative to the axis of the pipe. Furthermore imbedding the ultrasonic transducer in an epoxy resin subjects the transducer to mechanical stresses that results in decreased sensitivity. Finally, it was not possible to perform any calibration or operating checks on the transducer head before the transducers themselves were completely encapsulated within the head. After encapsulation, of course, it was not possible to make any changes to correct problems that would occur to make the transducer head inoperative.

BRIEF SUMMARY OF THE INVENTION

In order to overcome the foregoing disadvantages with respect to transducer heads, particularly for ultrasonic doppler flowmeters, a preformed transducer housing is utilized in which the housing may readily be made by the injection molding process. The housing is composed of a base member having a semi-cylindrical concave surface for engagement with the outer wall of a pipe. The concave outer surface is particularly desirable so that when the base is in contact with a pipe wall having a radius slightly greater than the radius of the semi-cylindrical surface of the transducer head, there is a small volume between the housing assembly and the pipe wall that terminates at line contacts between the edge of the base and the pipe wall. This small volume is preferably filled with an acoustic coupling agent to improve the coupling of the ultrasonic vibrations from the transducer head to the pipe wall. In order to accommodate pipes of significantly different radii while retaining a small gap between the pipe and the transducer housing assembly, a saddle is provided with a top convex surface of proper size and shape to mate with the bottom concave surface of the transducer head and a bottom concave surface of radius differing from the concave surface of the transducer head and forming a small volume void between the pipe and the head when mounted on a pipe. It is thus possible to use a single transducer head to fit a wide variety of pipe dimensions.

The transducer housing assembly also includes as a part thereof a pair of pedestals molded integrally with the base. Each pedestal is provided with a flat face which is angled with respect to the base and on which suitable ultrasonic transducers such as piezoelectric elements are mounted. Because of the integral relation between the base and the pedestals, the angle of the transducer with respect to the pipe is more precisely controlled than generally can be achieved with transducer housing assemblies of the prior art. Additionally, the two pedestals within the transducer housing are separated by an air gap from each other and also from the side walls of the housing assembly in order to minimize unwanted coupling between the transducers. Each of these features contributes to and provides an improved sensitivity of the transducer head assemblies of the prior art.

Additionally contributing to the improved sensitivity is the air backing for the transducers. With the present invention the transducers are secured by a biasing force to the flat face of the pedestals in such a way that the majority of the exposed side of the transducer is in contact with air. In the prior art encapsulated transducers, it was necessary to provide acoustic damping material on the face of the transducer away from the pipe. Finally the method of mounting the transducers permits a greased interface between the transducer and the surface of the pedestal. This avoids stresses that are produced when the transducer is secured by adhesive within the head. Such stresses tend to reduce the sensitivity of the apparatus.

In order to utilize the teachings of U.S. Pat. No. 4,208,908-Hickox, a well is provided within the transducer housing assembly for mounting a temperature sensitive element to provide a temperature responsive signal to compensate for changes in temperature of the transducer head. A sealed entrance chamber and a cover sealed on the top of the housing assembly provides a completely enclosed sealed environment for the transducers within the transducer head assembly. The sealing of the head assembly is accomplished after full testing of the head has been completed to establish that the transducer head is operative.

BRIEF DESCRIPTION OF THE DRAWINGS

In the plan view of FIG. 1 there is shown an ultrasonic doppler flowmeter head 10 mounted on the side of a pipe 12 by means of a clamping strap 14. A clamp tightening mechanism 16 for the strap 14 is shown in more detail in the end elevation of FIG. 2. It is to be understood that while a conventional hose clamp has been illustrated, that any clamping device may be used to secure the transducer head 10 to the outer wall of the pipe 12. As shown in FIG. 1, the transducer head 10 consists of a transducer housing 18 having a base member 20 with a pair of upstanding sidewalls 22,22 an end wall 24, and a second end wall 26 through which passes an electrical cable 28. The transducer head 10 is completely enclosed by a cover 30 engaging the exposed edges of the sidewalls 22,22 and the end walls 24,26.

Figure 1:
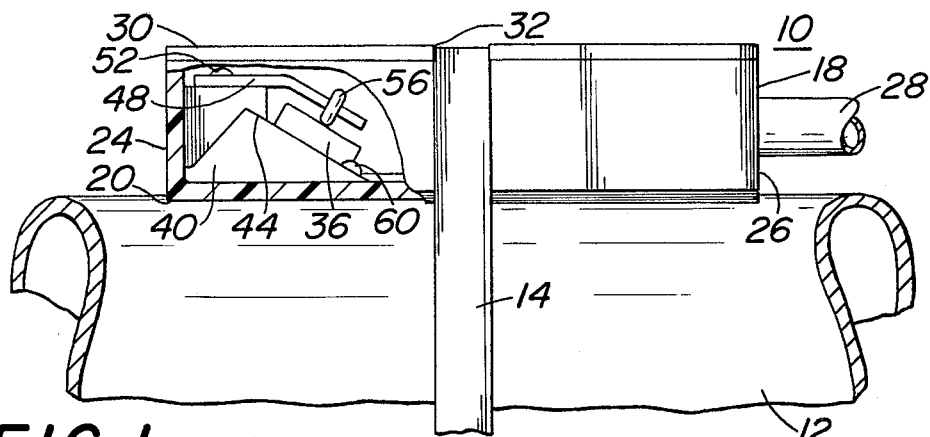
FIG. 1 is a plan view showing a transducer head assembly attached to the wall of a pipe.

The cover 30 is provided with a notch 32 into which the clamping strap 14 is placed to prevent the strap 14 from slipping with respect to the transducer head 10 when the clamp tightening mechanism 16 is operated to secure the transducer head 10 to the outer wall of the pipe 12.

Figure 2:
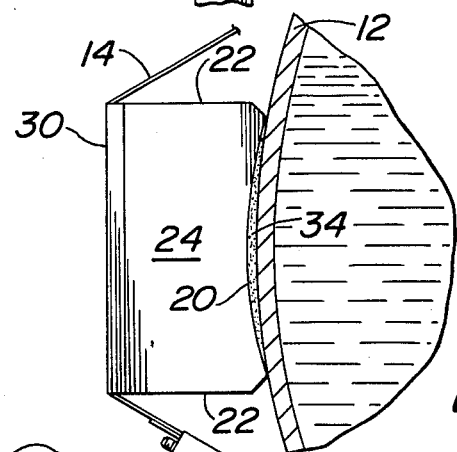
FIG. 2 is an end elevation of a transducer head attached to the wall of a pipe.

As shown more particularly in FIG. 2, the base member 20 of the transducer housing 18 has a semi-cylindrical concave outer surface. The radius of this semi-cylindrical surface is preferably slightly smaller than the radius of the outer wall of the pipe 12 to which the transducer head 10 is clamped. With this arrangement it will be noted that the transducer head 10 will be substantially supported on the outer wall of the pipe 12 along two parallel lines at the outer edge of the base 20. Disposed between these two supporting lines is a small volume having a cross section area as shown in FIG. 2. This volume is filled with an acoustic coupling material 34 of any conventional type when the transducer head 10 is mounted on the outer wall of the pipe 12. With the construction as shown it will be apparent that the coupling material 34 will only be able to escape from the small volume through its open ends. With this limited egress, the coupling material 34 does not tend to bleed out from the small volume and thus the ultrasonic waves generated in the transducer head 10 are readily coupled, without significant loss, to the wall of the pipe 12. In addition to the advantage of preventing loss of coupling material, there is no tendency for the transducer head 10 to rock on the outer surface of the pipe 12 as the clamp tightening mechanism is operated to securely clamp the transducer head 10 to the pipe 12. Also with the head 10 supported by the edges of the base 20, the head 10 will by definition be maintained in parallel relation with respect to the pipe 12.

The transducer head 10 as shown in FIG. 1 is partially in section to disclose the internal mounting of an ultrasonic transducer 36 within the transducer head 10. The base 20 of the transducer housing 18 is provided with a pedestal 40 integrally formed with the base 20. The pedestal 40 is provided with a sloping flat face 44 which forms an angle with the base 20 and therefore with the axis of the pipe 12. Mounted on the sloping flat face 44 is the ultrasonic transducer 36. In order to improve the acoustic coupling from the transducer 36, a coating of acoustic coupling grease may be applied to the sloping flat face 44 before the ultrasonic transducer 36 is placed in position. As shown, the ultrasonic transducer 36 is held in place on the sloping flat face 44 by means of a bias force applied to the exposed face of the ultrasonic transducer 36 by a cantilevered arm 48 secured to the pedestal 40 by means of a screw 52. Mounted on the distal end portion of the cantilevered arm 48 is an "O" ring 56 which is compressed between the exposed face of the ultrasonic transducer 36 and the surface of the cantilevered arm 48 to provide the bias force necessary to maintain the ultrasonic transducer 36 in position on the sloping flat face 44. In order to prevent the ultrasonic transducer 36 from sliding along the surface of the sloping flat face 44, a pair of protuberances 60,60 are located on the sloping flat face 44 to form mechanical stops for the transducer 36.

Figure 3:
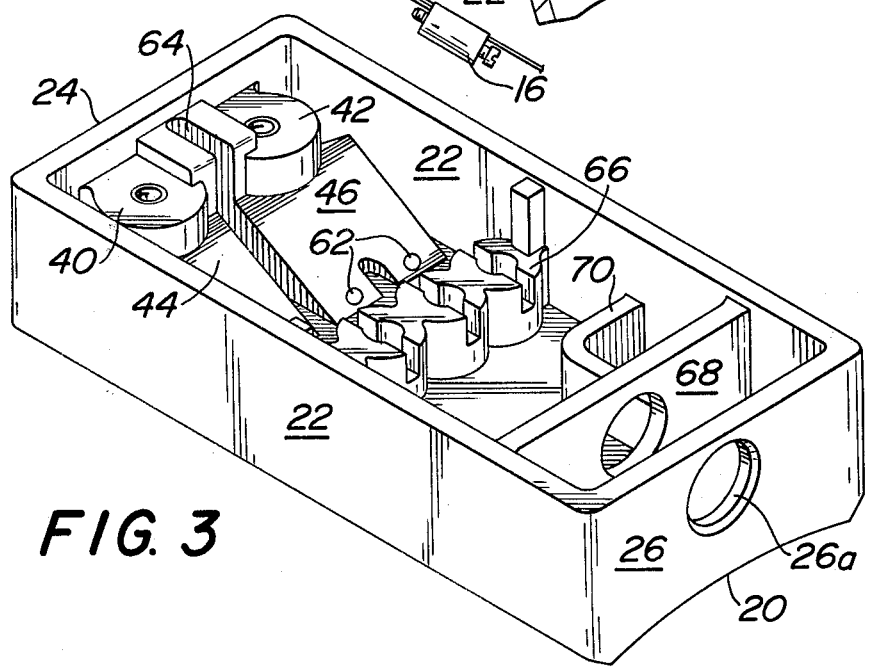
FIG. 3 is an isometric view of the preformed transducer housing.

The details of the transducer housing 18 are more clearly shown in the isometric drawing of FIG. 3. The transducer housing 17 may be made of any suitable material having good acoustic transmission properties. A material that has been found to be well suited for this use is a poly(amide-imide) identified as Torlon Grade 4203L available from Amoco Chemicals Corporation which can readily be made in the form of the transducer housing by the injection molding process.

FIG. 3 not only shows the base member 20 with the pedestal 40, and the sloping flat face 44, but also shows a second pedestal 42 with a corresponding sloping flat face 46 having a pair of protuberances 62,62 for mounting of a second transducer 38. It will be noted from FIG. 3 that the pedestals 40 and 42 are laterally separated from each other by an air gap 64 and is similarly separated from the sidewalls 22,22 by gaps. In ultrasonic doppler flowmeters utilizing amplitude modulation detection of the doppler signal it is necessary to have a coupling of the transmitted signal directly from the transmitter to the receiver. While this coupling of the transmitted signal often results from acoustic coupling between the transmitting transducer and the receiving transducer, a more reliable result may be achieved if such coupling is obtained by controlled electrical coupling rather than by unavoidable coupling through the material of the transducer head. The air gap 64 between the two pedestals 40 and 42 is particularly desirable to improve the sensitivity of the ultrasonic transducer head 10 by reducing the unavoidable coupling and replacing it with controlled electrical coupling.

In the ultrasonic doppler flowmeter, changes in the angle at which the transducer is mounted varies transfer function and the sensitivity and thus the performance of the transducer head. With the arrangement as shown, because the flat faces 44 and 46 are precisely oriented, there is less likelihood of improper orientations of the transducers when they are mounted on the sloping flat faces 44 and 46 in the manner described in this application.

Other features of the transducer housing assembly shown in FIG. 3 include a connection block 66 where connections between input leads and transducer leads are secured to eliminate the possibility of movement of the leads by mechanical shock during use. As shown a transverse wall 68 forms with the end wall 26 an enclosed entrance chamber that may be filled with a suitable sealing compound to seal the incoming cable 28 (FIG. 1) as it enters the transducer head 10. Located between the sidewall 22 and transverse wall 68 is a wall structure 70 that creates a well 72 into which may be secured a temperature sensitive electrical element for compensating the ultrasonic doppler flowmeter in accordance with the teachings of U.S. Pat. No. 4,208,908-Hickox.

Figure 6:
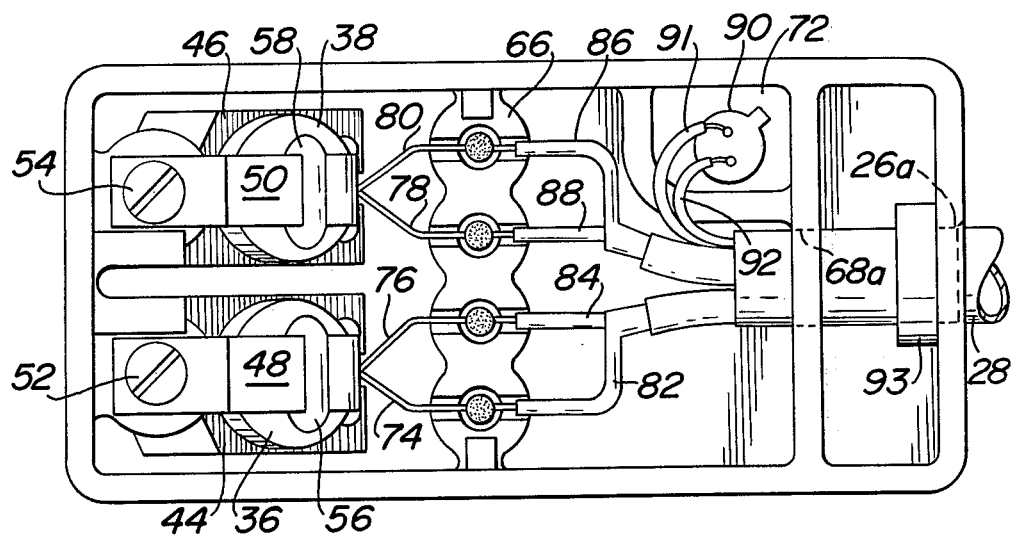
FIG. 6 is a plan view of the completed transducer head assembly with the cover removed.

FIG. 6 is a plan view of the transducer head 10 with the electrical components shown mounted in the head 10. The ultrasonic transducers 36 and 38 are shown mounted on the sloping flat faces 44 and 46. They are secured to the sloping flat faces 44 and 46 by the cantilevered arms 48 and 50 and their associated "O" rings 56 and 58. Electrical leads 74 and 76 are connected to opposite surfaces of the ultrasonic transducer 36 and electrical leads 78,80 are connected to opposite surfaces of the ultrasonic transducer 38. As shown, the electrical lead 74 is connected to a shield 82 of a shielded wire 84 which wire 84 is connected to the electrical lead 76. Similarly, a shield 86 of a shielded wire 88 is connected to the transducer lead 80 and the wire 88 is connected to the electrical lead 78. An electrical temperature responsive device 90 which may be a thermistor or a resistance thermometer is shown located in the well 72. Electrical leads 91 and 92 are shown connected to the electrical temperature responsive device 90. The shielded leads 84 and 88 together with leads 91 and 92 are formed together into the electric cable 28 which passes through a hole 68a in the transverse wall 68 and a hole 26a in the end wall 26. In order to secure the cable mechanically in place, a collar 93 may be attached to the outer covering of the cable 28 to engage with the inner surface of the hole 26a. Additionally, the entrance chamber formed between the transverse wall 68 and the end wall 26 may be filled with a sealing compound to protect the enclosed volume within the transducer housing 18 from adverse atmospheric conditions.

Figure 4:
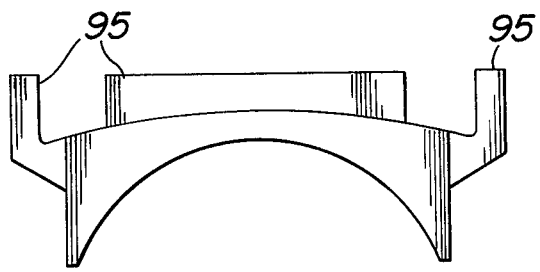
FIG. 4 is an end elevation of a saddle for use with the transducer head assembly.
Figure 5:
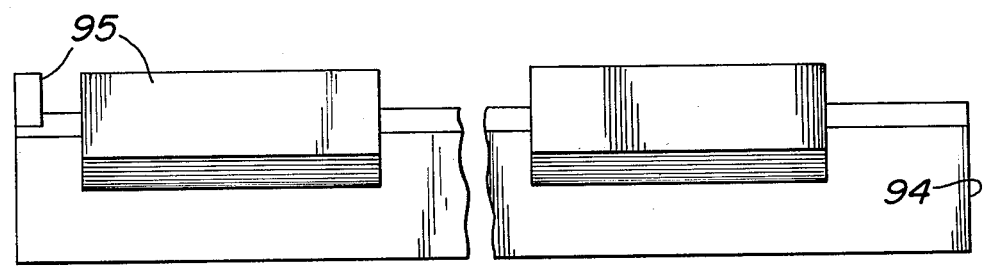
FIG. 5 is a side elevation of the saddle.

As has previously been indicated, the base 20 of the transducer housing 18 is provided with a concave semi-cylindrical surface for engaging the outer surface of the wall of the pipe to which the transducer housing is secured. For situations in which the radius of curvature of the base 20 is greater than the radius of curvature of the pipe 12, the transducer housing 18 would then contact the outer surface of the wall of the pipe along a single line element which could adversely affect the operation of the ultrasonic doppler flowmeter in the manner as previously described when a transducer head having a flat face was clamped to a round pipe. In order to eliminate this problem, and also to avoid the necessity of producing transducer heads having different radii, a saddle 94 may be used in conjunction with the transducer head 10. The saddle 94 is shown in FIGS. 4 and 5 and comprises a solid block of material preferably of the same composition as used for the transducer housing 18 having a convex semi-cylindrical surface of radius equal to the radius of the concave surface on the base 20 of the transducer housing 18. The saddle 94 has an opposing concave semi-cylindrical surface of a radius smaller than the radius of its convex surface. With this saddle arrangement, the transducer head 10 is secured to the convex surface of the saddle 94 and mates perfectly therewith. The concave surface of the saddle 94 then permits the transducer head assembly 10 to be used with pipes having smaller diameters but avoids the single line contact discussed above and provides the same advantages as when the head 10 is used with pipes of larger diameter and is supported on the pipe by two line contacts. In order to help secure the transducer head to the saddle 94, the saddle 94 is provided with a plurality of upstanding projections 95 along the edges and at one end of the convex surface of the saddle 94. The projections 95 along the edges of the saddle 94 are preferably spaced apart a distance equal to the width of the transducer housing 18.

While the term "clamp on" has been used throughout the specification in referring to the transducer head 10, it is to be understood that this generically means that the head 10 is adapted to be mounted on the outer surface of the wall of the pipe 12. The head 10 may be secured to this outer surface by any means including a mechanical clamping device or by a suitable adhesive without departing from the scope of the invention. The term "clamp on" was used merely to distinguish from those applications in which the ultrasonic transducer head intrudes into the pipe to perform its measuring function.

In a preferred embodiment of the invention the transducer head has been made by injection molding of a poly(amide-imide), the invention is not limited to the method of manufacture nor to the material. Other materials such as glass or the material of the pipe in which the fluid is flowing could be used and the transducer head could be formed by casting or compression molding.

What is claimed is:

1. A preformed transducer housing for an ultrasonic flowmeter for mounting on the outer surface of a cylindrical pipe comprising:
   a base member having a semi-cylindrical concave surface for engagement with said surface of said pipe;
   side walls and end walls carried by said base member upstanding away from said semi-cylindrical surface to form an enclosure;
   pedestal means integral with said base member located within said enclosure, said pedestal means having an exposed flat face, the plane of said face forming an acute angle with the axis of said semi-cylindrical surface, and
   acoustic transmission barrier means in said pedestal means for dividing said exposed flat face into two areas separated by said acoustic transmission barrier means.

2. A preformed transducer housing assembly for a clamp-on ultrasonic flowmeter having a transmitting transducer and a receiving transducer comprising:
   a base member having a concave semi-cylindrical surface;
   upstanding side walls and end walls carried by said base member and forming with said base member an enclosure;
   first and second pedestals carried by said base member, each of said pedestals having a sloping flat face in the form of a plane surface forming an acute angle with the axis of said semi-cylindrical surface;
   means located between said pedestals to provide an acoustic transmission barrier between said pedestals;
   a cover for engaging the exposed edges of said upstanding walls to form a completely enclosed volume, and
   means for providing an electrical connection to said transducers within said enclosed volume.

3. A transducer housing assembly as claimed in claim 2 in which said means to provide said acoustic transmission barrier is an air space between said pedestals.

4. A transducer housing assembly as claimed in claim 3 in which said pedestals are isolated from said side walls by an air space.

5. A transducer housing assembly as claimed in claim 3 in which said pedestals are integral with one of said end walls of said enclosure and said flat faces on said pedestals lie within a single plane.

6. A transducer housing assembly as claimed in claim 5 in which said means for providing for electrical connection is an opening in the other of said end walls.

7. A transducer housing assembly as claimed in claim 6 including an upstanding transverse wall having an opening therethrough located adjacent to said other end wall.

8. A transducer housing assembly as claimed in claim 3 including a well structure integral with said base for holding a temperature sensing element therein.

9. A molded transducer head for an ultrasonic doppler flowmeter including a base member having:
   a semi-cylindrical concave surface;
   first and second pedestals integral with said base member;

a sloping plane face formed in each of said pedestals at an acute angle to the axis of said semi-cylindrical surface;

a piezoelectric element mounted on each of said faces, and resilient means for applying a force to said element to hold said element on said face.

10. A transducer head as set forth in claim 9 in which said last named means comprises:

a cantilevered arm carried by said pedestal and spaced from said element, and spring bias means located between said arm and said piezoelectric element.

11. A transducer head as claimed in claim 10 in which said spring bias means is an "O" ring surrounding said cantilevered arm and compressed between said arm and said piezoelectric element.

12. A transducer head as claimed in claim 11 in which said transducer head is injection molded of a poly(amide-imide).

13. An improved injection molded high temperature transducer head for a clamp-on ultrasonic doppler flowmeter for measuring flow in a pipe comprising:

a base having a semi-cylindrical concave surface having a first radius of curvature;

sidewalls and end walls upstanding from and integral with said base member to form an enclosure;

first and second pedestals within said enclosure upstanding from and integral with said base and integral with one of said end walls;

acoustic barrier means comprising an air space between said pedestals and between each said pedestal and its adjacent sidewall;

a flat face in each said pedestal, both said flat faces lying within a single plane forming an acute angle with the axis of said semi-cylindrical concave surface;

first and second piezoelectric elements mounted respectively on said flat faces of said first and second pedestals and having exposed surfaces;

an acoustic coupling agent between said elements and their respective flat faces;

first and second cantilevered arms secured respectively to said first and second pedestals, said arms having their distal portions parallel to said flat faces;

first and second "O" rings surrounding said distal portions of said cantilevered arms and respectively engaging said exposed surface of said first and second elements;

electrical temperature responsive means for producing an electrical signal varying with the temperature of said transducer head;

a well structure integral with said base forming a well for holding said electrical temperature responsive means;

electrical leads for said piezoelectric elements and said electrical temperature responsive means;

a transverse wall integral with said side walls and said base and spaced from the other of said end walls to form an entrance chamber;

a first opening through said other end wall for passage of said electrical leads through said end wall;

a second opening through said transverse wall for passage of said electrical leads through said transverse wall;

means in said entrance chamber for securing said leads to said transducer head and to seal said openings, and a cover for engaging the exposed edges of said end walls and said sidewalls to form a completely enclosed volume, said cover having an external area for engaging a clamping device.

14. A transducer head as set forth in claim 13 including a solid saddle member having a length and width to match the length and width of said base, a semi-cylindrical convex surface of said first radius of curvature secured to said concave surface of said base and an opposing semi-cylindrical concave surface of a second radius of curvature less than said first radius of curvature.

* * * * *